United States Patent [19]
Ochi et al.

[11] Patent Number: 5,110,386
[45] Date of Patent: May 5, 1992

[54] METHOD OF FORMING PARTS OF PRODUCTS TO BE WORN

[75] Inventors: Mitsuzo Ochi, Ehime; Shoji Nakano, Kanonji; Masashi Hosokawa, Kagawa, all of Japan

[73] Assignee: Uni-Charm Corporation, Ehime, Japan

[21] Appl. No.: 515,126

[22] Filed: Apr. 27, 1990

[30] Foreign Application Priority Data

Apr. 29, 1989 [JP] Japan .................. 1-111698

[51] Int. Cl.$^5$ .................. B32B 31/08; A61F 13/15
[52] U.S. Cl. .................. 156/204; 156/265; 604/385.1
[58] Field of Search .................. 156/265, 256, 201, 88, 156/204; 604/385.1, 385.2

[56] References Cited

U.S. PATENT DOCUMENTS

| | | | |
|---|---|---|---|
| 2,744,844 | 5/1956 | Wood, Jr. et al. | 156/88 X |
| 2,988,457 | 6/1961 | Gatcomb | 156/88 X |
| 3,755,033 | 8/1973 | Emus | 156/88 |
| 3,816,227 | 6/1974 | Schaar | 156/196 X |
| 3,984,272 | 10/1976 | Teed | 156/201 |
| 4,124,423 | 11/1978 | Zabron et al. | 156/88 |
| 4,557,777 | 12/1985 | Sabee | 156/256 X |
| 4,595,441 | 6/1986 | Holvoet et al. | 156/265 |
| 4,690,719 | 9/1987 | Lucas et al. | 156/201 |
| 5,034,007 | 7/1991 | Igaue et al. | 604/385.1 |

FOREIGN PATENT DOCUMENTS 62-231659 10/1987 Japan .
62-250202 10/1987 Japan .

*Primary Examiner*—Michael W. Ball
*Assistant Examiner*—Adrienne Johnstone
*Attorney, Agent, or Firm*—Fred Philpitt

[57] ABSTRACT

The present invention pertains to a method wherein a concavoconvex cutting line is applied repetitively in a periodical way in the longitudinal direction of a continuous first web to form first and second partial webs; said first partial web is offset with respect to said second partial web in the longitudinal direction by a prescribed interval so that the concave edges and the convex edges of the first and second partial webs are positioned opposite to and aligned with each other, whereafter a continuous second web is used to connect the outside edges opposite to the said aligned concave and convex edge portions of the first and second partial webs, and as the second web is bonded with the outside edges of the partial webs a composite web is formed, following which the first and second partial webs of the composite web are spread apart.

4 Claims, 4 Drawing Sheets

METHOD OF FORMING PARTS OF PRODUCTS TO BE WORN

THE INVENTION GENERALLY

This invention concerns a manufacturing method of the structural parts for wearing products. More specifically, it concerns a manufacturing method of the structural parts of disposable diapers, baby training pants, or other wearing products.

BACKGROUND

In the conventional manufacturing method of disposable wearing products, in order to cut the manufacturing cost by reducing waste in the materials, a continuous web is cut along the longitudinal central line to form symmetric concavoconvex edge portions. Then, the partial webs are cut at the prescribed length to form the structural parts, such as disclosed in Japanese Kokai Patents Nos. Sho 62[1987]-231659 and Sho 62[1987]-250202.

In the former specification, it is indicated that the said partial webs are assembled as the tape fastener of the disposable diaper. However, there is no specific description of this method.

In the latter specification, it is pointed out that the said partial webs are used to form the die-shaped [sic] absorptive body which is used to assemble the disposable diaper. In this scheme, one of the pair of partial webs having concavoconvex edge portions makes a rotation around and oblique roll so that it is offset from the other web; in this way, with the concavoconvex edge portions of the webs located on the outsides and symmetric to each other, they are laminated with each other, followed by cutting at prescribed positions in the transverse direction to form the die-shaped absorptive body.

However, in the scheme disclosed in the latter specification, as one of the partial webs is made to rotate 1 cycle on an oblique roll so that it is offset with respect to the other partial web, the interval alignment is difficult because the said partial web may easily slide in the axial direction on the roll. Besides, when twisting takes place for one partial web, the other partial web may be entangled with the first partial web. Hence, it is still a topic to be solved for incorporating these webs at a high speed with the other structural parts.

OBJECTS

The purpose of this invention is to provide a manufacturing method of the structural parts of the wearing product characterized by the following features: for a pair of partial webs, one web is offset with respect to the other web without twisting or entangling with each other; the concave edge portions and the convex edge portions of these webs are made opposite and aligned to each other, respectively; with these aligned concavoconvex portions of the webs arranged on the outsides, the wearing product is manufactured.

SUMMARY OF THE INVENTION

In order to realize the aforementioned purpose, in the method of this invention, a concavoconvex cutting line is applied repetitively in a periodical way in the longitudinal direction of a continuous first web to form the first and second partial webs; the said first partial web is offset with respect to the said second partial web in the longitudinal direction by a prescribed interval, so that the concave edges and the convex edges of the first and second partial webs are positioned opposite and aligned to each other, respectively. Then, a continuous second web is used to connect the outside edges opposite to the said aligned concave and convex edge portions of the first and second partial webs; as the second web is bonded with the outside edges of the partial webs, a composite web is formed; the first and second partial webs of the composite web are spread to the outer sides.

When the said first and second partial webs are bonded with the said second web, a fold-back portion can be formed at each outside edge portion of the second web and the formed fold-back portions are bonded with the outside edges of the first and second partial webs; it is also possible to form fold-back portions at the outer edge portions of the first and second partial webs and to bond these fold-back portions with the outside edge portions of the second web.

It is preferred that the said first partial web be offset by a prescribed interval in the longitudinal direction with respect to the said second partial web to ensure alignment between the opposite concave edge portions and between the opposite concave edge portions of the first and second partial webs by arranging a roller with a prescribed diameter at a position in the direction perpendicular to the transfer plane of the second partial web with a prescribed vertical difference and at a right angle to the transfer direction of the first and second partial web and making the first partial web go through this roller.

DESCRIPTION OF PREFERRED EMBODIMENTS

In the following, the application examples of the method of this invention will be explained with reference to figures.

Figure 1:
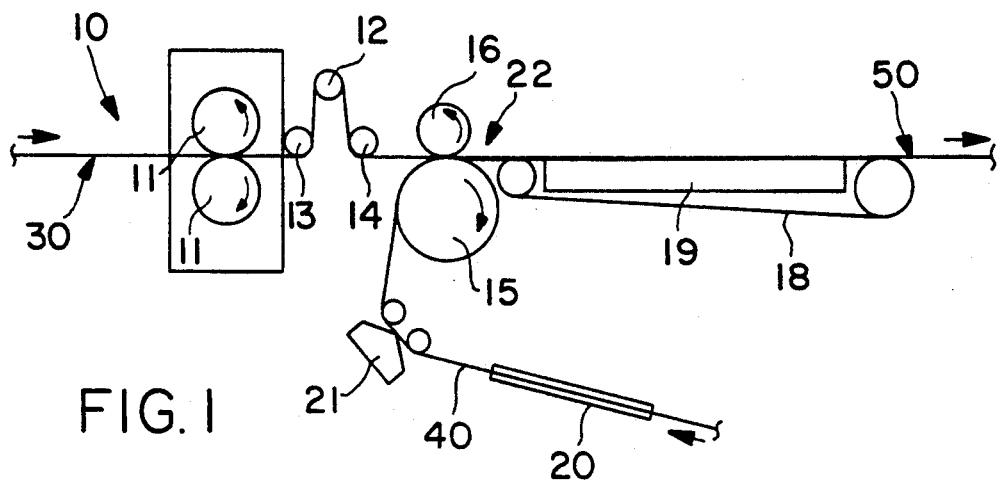
FIG. 1 is a schematic side view of the apparatus for implementing the method of this invention.
Figure 2:
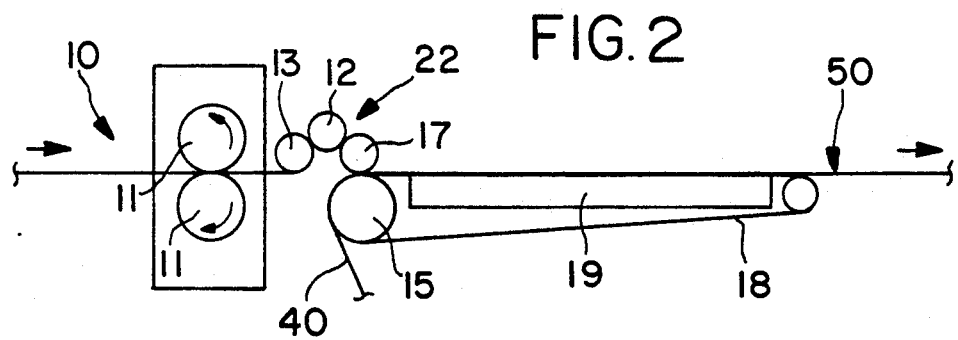
FIG. 2 is a schematic side view of another apparatus for implementing the method of this invention.
Figure 3:
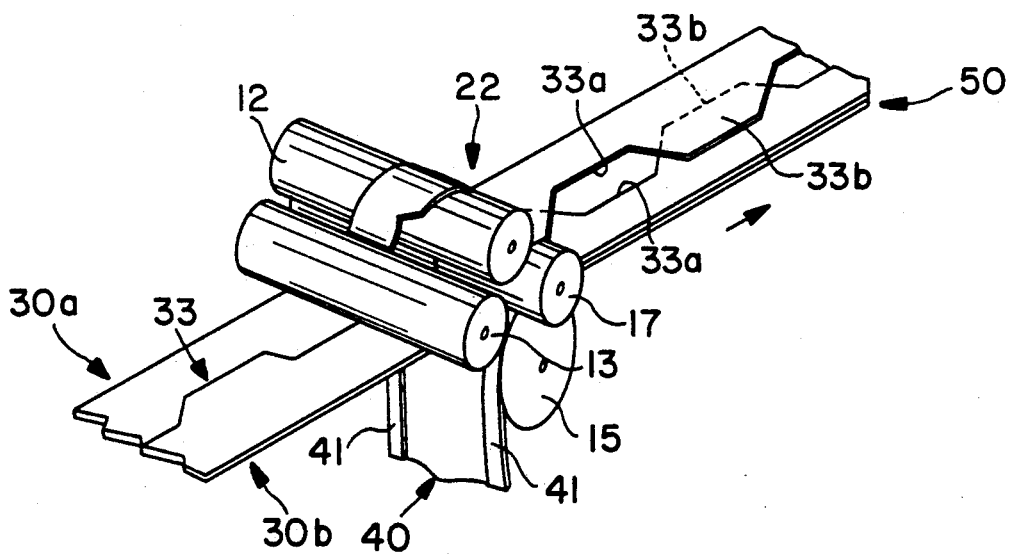
FIG. 3 is an oblique view of a portion of the apparatus shown in FIG. 2.

FIGS. 1-3 schematically illustrate apparatus (10) for implementing the method of this invention. In apparatus (10) shown in FIG. 1, there are the following parts for processing continuous first web (30): roll cutter (11), guide rolls (12), (13), (14), bearing roll (15), and pressing roll (16). In apparatus (10) shown in FIG. 2, the following parts are used to process continuous first web (30): roll cutter (11), guide rolls (12), (13), and guide/pressing roll (17). In apparatus (10) shown in FIG. 1, guide roll (12) is arranged at a certain distance above guide rolls (13), (14) which are arranged opposite to each other at a certain distance. On the other hand, in apparatus (10) shown in FIG. 2, guide roll (12) is arranged in contact with or near guide roll (13) and pressing roll (17) which are located opposite to each other at a certain distance. For apparatus (10) shown in FIG. 1 and that shown in FIG. 2, the processing operation schemes of the continuous first web (30) are substantially the same. In order to process continuous first web (30) and continuous second web (40), in addition to said bearing roll (15) and said pressing rolls (16) and (17), apparatus (10) also contains a porous belt conveyor (18), a suction unit (19), a bending guider (20), and a coating unit (21). FIG. 3 illustrates a portion of apparatus (10) shown in FIG. 2.

Figure 4:
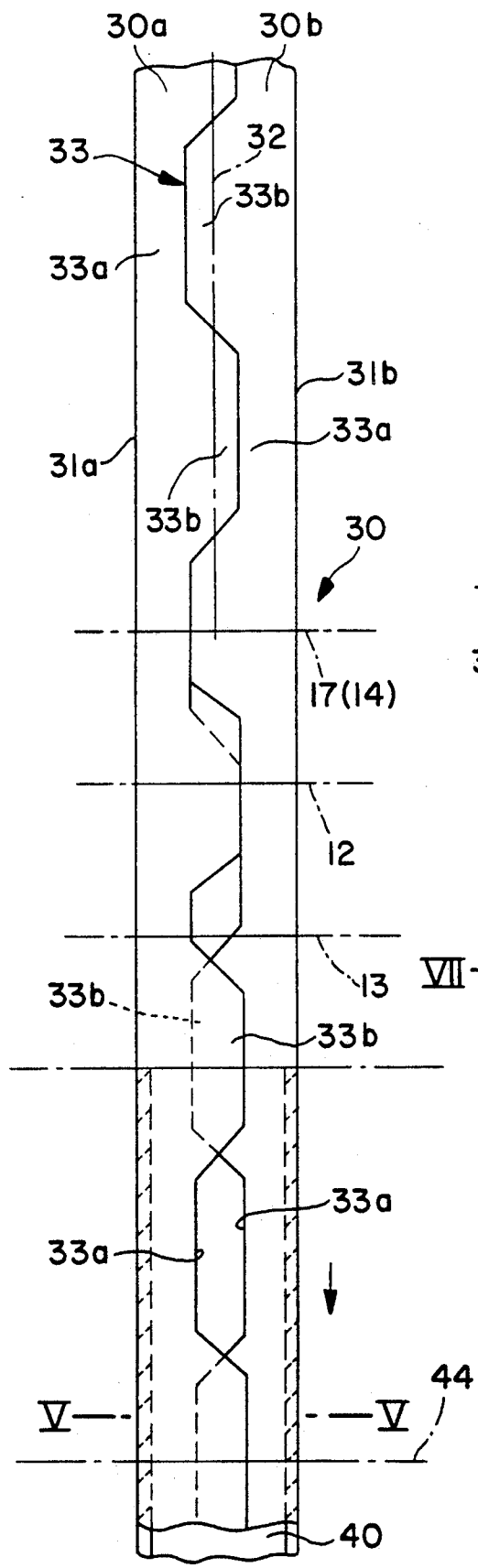
FIG. 4 is a plane view showing the state of aligned opposite concave and convex edges of the first and second partial webs formed by cutting along the concavoconvex cutting line running along the longitudinal central line of the first web in a symmetric way.

As shown in FIG. 4, continuous first web (30) has substantially parallel side edges 31a), (31b); with respect to longitudinal central line (32) cutting line (33) for forming concavo-convex portions is drawn repetitively in a periodical way along the longitudinal direction, so that the first web is cut by said roll cutter (11) to form first division web (30a) and [second partial web] (30b) having concave edge portions (33a) and convex edge portions (33b).

As shown in FIG. 3 (also see FIGS. 1 and 2), first partial web (30a) is made to pass above guide roll (12) and below guide roll (13) and pressing roll (17). In this way, it is separated from second partial web (30b). At the same time, as it is transferred to bonding station (22) containing bearing roll (15) and pressing roll (16), it is offset in the longitudinal direction by an interval of $(\frac{1}{2})n$ (where n is an odd number) with respect to second partial web (30b). In this way, concave edge portions (33a) as well as convex edge portions (33b) of the first and second partial webs (30a), (30b) are made opposite and aligned with each other, respectively. In this case, opposite convex edge portions (33b) are laminated. In this way, the interval of offset of the first partial web (30a) with respect to second partial web (30b) in the longitudinal direction can be determined by the diameter of guide roll (12) and the height of guide roll (12) above the transfer plane of second partial web (30b). In the application example, it is preferred that guide roll (12) be rotated. However, it is also possible to arrange guide roll (12) separately without coupling to other rolls by contact between peripheries. In this case, the guide roll may not be rotatable.

Figure 5:
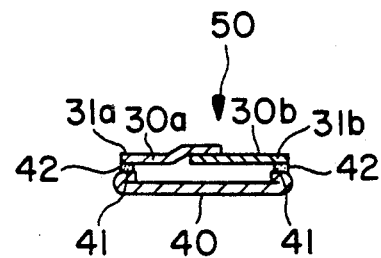
FIG. 5 is a cross-sectional view cut along the V—V line in FIG. 4.
Figure 6:
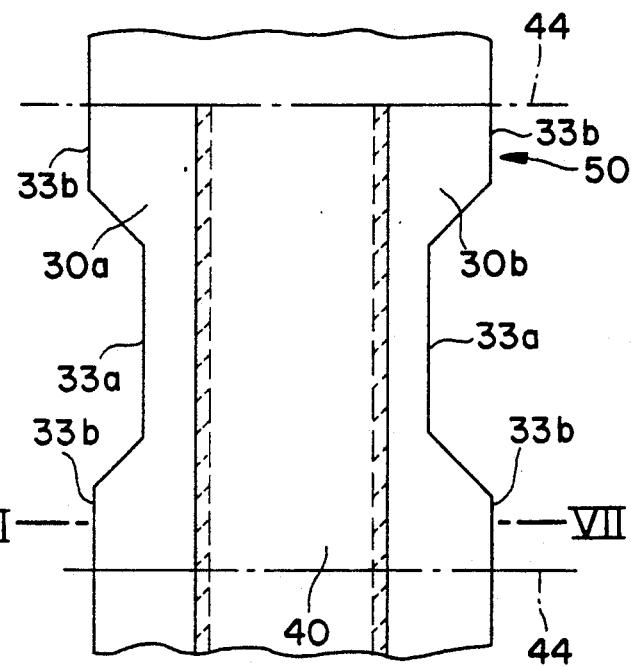
FIG. 6 is a plane view illustrating the state of the composite web in FIG. 4 with portions of it spread outwards.
Figure 7:
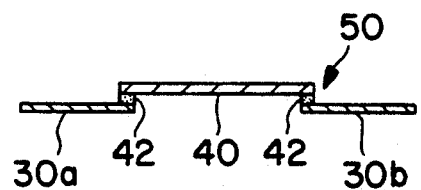
FIG. 7 is a cross-sectional view cut along VII—VII line in FIG. 6.

On the other hand, in folding guider (20), second web (40) has its two sides folded back to the upper surface. After adhesive (42) is coated on fold-back portions (41) by coating unit (21), it is located below said aligned first and second partial webs (30a), (30b); these webs are made to pass between bearing roll (15) and pressing roll (12) [sic] together. After this passage, as shown in FIG. 5, outside edges (31a), (31b) of first and second partial webs (30a), (30b) are bonded with fold-back portions (41) of second web (40) by adhesive (42). In this way, a continuous composite web (50) is formed from first and second partial webs (30a), (30b) and second web (40). As composite web (50) is transferred to the next stage for processing on belt conveyor (18), first and second partial webs (30a), (30b) are spread outwards by a spreading unit (not shown in the figure) arranged on belt conveyor (18) near the downstream side of bonding station (22), as shown in FIGS. 6 and 7.

The composite web (50) that can be manufactured using this scheme can be used as the structural part of wearing products, such as top sheet, back sheet, mat-like core, etc., of disposable diapers. It is well-known that the top sheet is made of nonwoven fabric, porous plastic film, or other thin soft and liquid permeable materials; the back sheet is made of plastic film, laminate of plastic film and nonwoven fabric, or other thin soft and liquid barrier materials; and the mat-like core is made of fluffy pulp, mixture of pulp and high-absorptivity polymer powder, or other relatively thick elastic and liquid absorptive materials. When composite web (50) is used as these structural parts, the first and second partial webs (30a), (30b) and second web (40) may be made of materials having different properties.

Figure 8A:
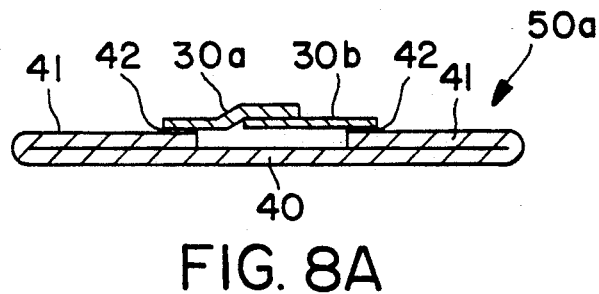
FIGS. 8A, 8B, 8C and 8D are also cross-sectional views similar to FIG. 5 illustrating other examples of composite webs.
Figure 8B:
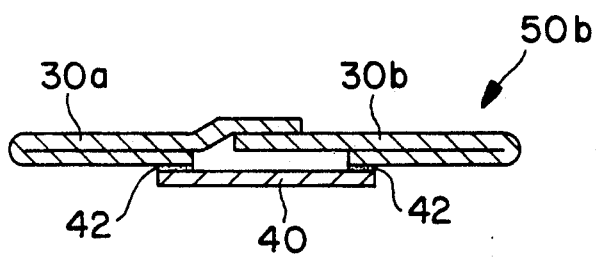
Figure 8C:
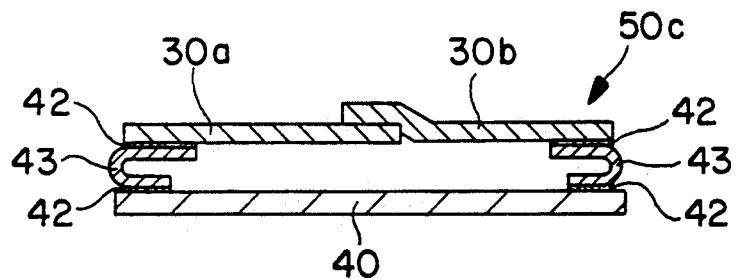
Figure 8D:
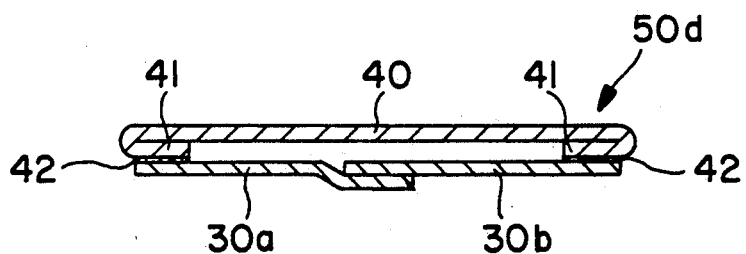
Figure 9:
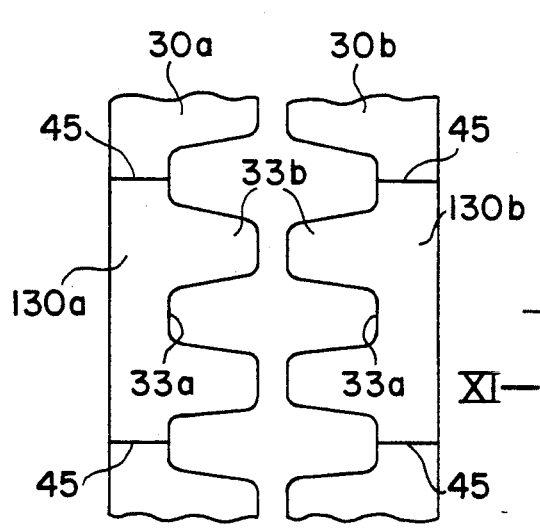
FIG. 9 is a plane view illustrating the composite web of the first and second webs used as the tape fastener of a disposable diaper.
Figure 10:
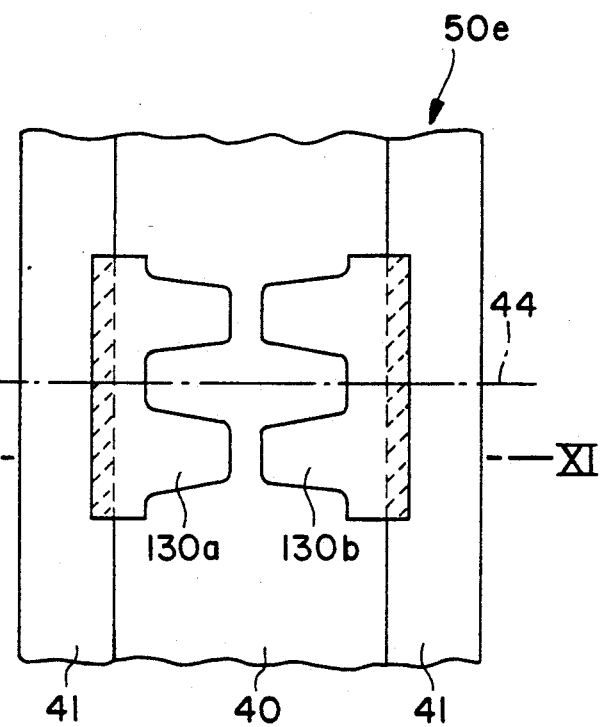
FIG. 10 is a partial plane view of the composite web cut to a prescribed length used as the tape fastener shown in FIG. 9 and bonded with the second web.
Figure 12:
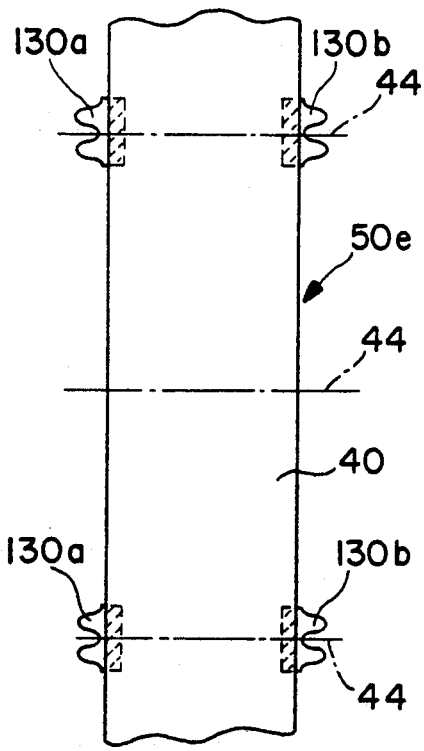
FIG. 12 is a plane view illustrating the state of the composite web shown in FIG. 10 with the fold-back portions spread outward together with the tape fasteners.
Figure 11:
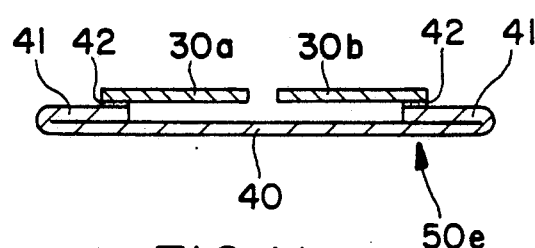
FIG. 11 is a cross-sectional view cut along the XI-XI line in FIG. 10.

FIGS. 8A-8D illustrate some variation examples of the composite web before spreading, manufactured either by the said apparatus (10) in its original form or by an apparatus with positions changed partially from that of apparatus (10). In these figures, as the parts and portions indicated by the same symbols as in said composite web (50) are identical or similar to those of the said composite web, only a minimum explanation for composite webs (50a), (50b), (50c), (50d) will be presented. Their manufacturing methods are essentially identical to the manufacturing method of said composite web (50). For composite web (50a) shown in FIG. 8A, compared with first and second partial webs (30a) and (30b), second web (40) and fold-back portions (41) are formed wider. For composite web (50b) shown in FIG. 8B, compared with second web (40), first and second partial webs (30a), (30b) are formed wider, and the two side portions of these partial webs are folded back to the lower surface and bonded with second web (40). For composite web (50c) shown in FIG. 8C, relatively thick first and second webs (30a), (30b) are connected to relatively thick second web (40) via folded ribbon sheets (43) made of a thin nonwoven fabric which are bonded with them. For composite web (50d) shown in FIG. 8D, first and second partial webs (30a), (30b) are located below second web (40). The composite webs (50a), (50b), and (50d) shown in FIGS. 8A, 8B, and 8D are suitable for applications as the top sheet and/or back sheet of a disposable diaper. The composite web (50c) shown in FIG. 8C is suitable for application as the mat-like core of a disposable diaper which has two side portions which are difficult to fold back.

When continuous composite webs (50) manufactured in the aforementioned scheme are used as, say, the top sheet and back sheet of the disposable diaper (in this case, although not shown in the figures, apparatus (10) has a structure enabling manufacture of continuous composite webs (50) as two rows with one above the other), mat-like cores formed separately are arranged between these sheets intermittently in sequence in the longitudinal direction; the peripheral portions of these sheets are bonded to form diaper laminates in a continuous way. Then, at prescribed positions of the laminate without core inserted, such as the positions indicated by the dash-dot lines in FIG. 6, the laminate is cut in the transverse direction to form individual diapers. For the top sheet and back sheet, it is also possible to use the following scheme: only one web is manufactured as a composite web (50), while for the other web, after the said laminate is formed, portions on its outer side are cut off in alignment with the concave edge portions of the first web. In addition, when composite web (50) is the core, composite web (50) can be cut beforehand at said positions (44) to form individual pieces, which are inserted between the top sheet and back sheet intermittently in the longitudinal direction to form the said laminate, which is then cut as mentioned above. In this manufacturing example, the overall configuration of the manufacturing system of diapers is able to form the top sheet and/or back sheet in the form of composite web (50), as apparatus (10) can be incorporated into the said system.

FIGS. 9-12 illustrate the example of using first and second partial webs (30a), (30b) as the pressing tape fasteners attached to the waistband of a disposable diaper. In this case, for first and second partial webs (30a), (30b), it is possible to align the opposite concave and convex edge portions (33a), (33b) manufactured using the said method (see FIG. 9). In this case, tape pieces (130a), (130b) are formed by cutting concave and convex edge portions (33a), (33b); for example, with a length containing two convex edge portions (33b), the partial webs are separated along central lines (45) at concave portions (33a). These tape pieces are bonded with adhesive (42) on fold-back portions (41) on the two sides of the back sheet or top sheet as the second web (40) to form composite web (50e) (see FIGS. 10 and 11). The position of bonding of tape pieces (130a), (130b) on second web (40) is at line (44) along which the individual diapers are to be cut out from the continuous diaper laminate prepared in the necessary process to form the end edges of the waistbands of the individual diapers. Hence, as the diaper laminate is cut to individual diapers along these lines, tape pieces (130a), (130b) are further divided to form the tape pieces for individual diapers.

ADVANTAGES OF THE INVENTION

According to the method of this invention, the first and second [partial] webs formed by dividing are positioned properly to ensure that the opposite concave edge portions as well as the convex edge portions positioned at the central portions of the said partial webs are aligned with each other, respectively; the outer edge portions of a second web are bonded with the outer edge portions of the aligned first and second partial webs to form a composite web; by spreading the first and second partial webs of the composite web outwards, the concave and convex edge portions are positioned on the outer sides. This scheme for positioning the opposite aligned concave and convex edge portions on the outsides is very simple.

In addition, fold-back portions are formed on the outer edges of the second web. The fold-back portions are bonded with the outer edges of the first and second partial webs. It is also possible to form the fold-back portions at the outer edges of the first and second partial webs, and to bond these fold-back portions to the second web. In this way, the said spreading operation can be carried out easily, and the finish of the said compound web is excellent.

In addition, a roller with a prescribed diameter is set above the transfer plane of the second partial web with a certain height in the vertical direction and at a right angle to the transfer direction of the first and second partial web. By making the first partial web go around this roller, the first partial web is offset with respect to the second partial web to ensure the alignment between the opposite concave and convex edge portions. In this way, without twisting the first web and without the need to cross the first and second webs, these webs can be assembled with other structural parts at a high speed in a stable way.

The method of this invention can be used for manufacturing various structural parts of wearing products, such as top sheets, back sheets, mat-shaped cores, tape fasteners, etc.

We claim:
1. The method which comprises the sequence of
   (a) subjecting an elongated continuous first web (30) having side edges (31a, 31b) to cutting in a longitudinal direction along an alternating concave convex cutting line between said side edges to thereby form a first partial web (30a) and second partial web (30b) that each have a series of alternating convex edge portions (33b) and a series of alternating concave edge portions (33a),
   (b) longitudinally offsetting said first and second partial webs (30a, 30b) with respect to each other so said convex edge portions (33b) at least partially overlay each other and said concave edge portions (33a) are at least partially spaced apart from each other,
   (c) providing a second web (40) having a main flat central section and two C-shaped side sections (41, 43) that face each other,
   (d) bonding the upper portions of said two C-shaped side sections (41, 43) to said side edges (31a, 31b) of said first web (30) while said convex edge portions (33b) remain overlapped to thereby form a composite web, and then
   (e) spreading apart said first and second partial webs (30a, 30b) through an arc of 180° so that the side edges (31a, 31b) of said first web (30) are disposed inwardly of said concave and convex edge portions (33a, 33b).

2. The method according to claim 1 wherein the two C-shaped side sections (41) in step (c) are folded over side portions of said second web (40).

3. The method according to claim 1 wherein the two C-shaped side sections (43) in step (c) are separate sections that have been bonded to the outer sides of said second web (40).

4. The method according to claim 1 wherein the offsetting in step (b) is accomplished by passing one of said cut partial webs (30a, 30b) over a guide roll (12) that temporarily moves said one partial web (30a) in a different path than the other partial web (30b).

* * * * *